(12) United States Patent
Fu et al.

(10) Patent No.: US 12,016,975 B2
(45) Date of Patent: Jun. 25, 2024

(54) IMPLANTABLE DEVICE

(71) Applicant: Biotyx Medical (Shenzhen) Co., Ltd, Shenzhen (CN)

(72) Inventors: Wenchao Fu, Shenzhen (CN); Wenjiao Lin, Shenzhen (CN); Li Qin, Shenzhen (CN)

(73) Assignee: Biotyx Medical (Shenzhen) Co., Ltd, Shenzhen (CN)

( * ) Notice: Subject to any disclaimer, the term of this patent is extended or adjusted under 35 U.S.C. 154(b) by 448 days.

(21) Appl. No.: 17/288,685

(22) PCT Filed: Oct. 14, 2019

(86) PCT No.: PCT/CN2019/110986
§ 371 (c)(1),
(2) Date: Apr. 26, 2021

(87) PCT Pub. No.: WO2020/108129
PCT Pub. Date: Jun. 4, 2020

(65) Prior Publication Data
US 2021/0393858 A1 Dec. 23, 2021

(30) Foreign Application Priority Data
Nov. 27, 2018 (CN) .......................... 201811425842.0

(51) Int. Cl.
*A61L 31/02* (2006.01)
*A61F 2/04* (2013.01)
*B22F 9/04* (2006.01)

(52) U.S. Cl.
CPC .............. *A61L 31/022* (2013.01); *A61F 2/04* (2013.01); *B22F 9/04* (2013.01);
(Continued)

(58) Field of Classification Search
None
See application file for complete search history.

(56) References Cited

U.S. PATENT DOCUMENTS 9,920,402 B2 3/2018 Lyon
2003/0083731 A1 5/2003 Kramer et al.
(Continued)

FOREIGN PATENT DOCUMENTS

CN 103371876 A 10/2013
CN 106367714 A 2/2017
(Continued)

OTHER PUBLICATIONS

Japanese Office Action dated May 10, 2022 in corresponding Japanese Application No. 2021549728; (10 pages, including English translation).
(Continued)

*Primary Examiner* — Kim S. Horger
(74) *Attorney, Agent, or Firm* — Maier & Maier, PLLC

(57) ABSTRACT

An implantable device including a metal substrate; that contains particles having a size of 1 μm or more; if the wall thickness of the metal substrate is greater than or equal to 0.04 mm and less than or equal to 0.12 mm, the largest particle size is less than or equal to 15 μm and the average content of the particles is less than or equal to 40 ppm; if the wall thickness of the metal substrate is greater than 0.12 mm and less than or equal to 0.2 mm, the largest particle size is less than or equal to 20 μm and the average content of the particles is less than or equal to 100 ppm; The size of the particles and the average content of the particles are reasonably controlled according to the wall thickness of the metal substrate, improving the plastic deformation capability of the implantable device.

10 Claims, 3 Drawing Sheets

(52) U.S. Cl.
CPC ... *A61F 2002/041* (2013.01); *A61F 2002/044* (2013.01); *A61F 2002/047* (2013.01); *B22F 2009/046* (2013.01); *B22F 2301/35* (2013.01)

(56) References Cited

U.S. PATENT DOCUMENTS

| | | | |
|---|---|---|---|
| 2008/0249607 A1* | 10/2008 | Webster | A61L 31/022 623/1.15 |
| 2009/0165898 A1* | 7/2009 | Wong | A61L 31/14 623/1.18 |
| 2010/0168841 A1 | 7/2010 | Furst et al. | |
| 2021/0393858 A1 | 12/2021 | Fu et al. | |

FOREIGN PATENT DOCUMENTS

| | | |
|---|---|---|
| CN | 109310493 A | 2/2019 |
| JP | 2006051353 A | 2/2006 |
| JP | 2013524004 A | 6/2013 |
| WO | 2017/184750 A1 | 10/2017 |
| WO | 2017/204803 A1 | 11/2017 |

OTHER PUBLICATIONS

Indian Office Action dated Jun. 24, 2022 in corresponding Indian Application No. 202127023093; 6 pages.
Chinese Office Action dated Jan. 6, 2021 in corresponding Chinese Application No. 201811425843.0; 12 pages.
He Qubo, et al., "Effect of VIM-ESR-VAR Triplex Melting Process on Cleanliness of Bearing Steel 9Cr18No", Special Steel, vol. 39, No. 1, Feb. 28, 2008, 11 pages.
International Search Report dated Feb. 6, 2020 in corresponding International Application No. PCT/CN2019/110986; 4 pages.
Chinese Office Action dated Jun. 9, 2021, in connection with corresponding CN Application No. 201811425843.0 (9 pp., including machine-generated English translation).
Office Action dated May 3, 2023, in corresponding Korean Application No. 10-2021-7019367, 10 pages.
Office Action dated Jul. 20, 2023, in corresponding Korean Application No. 10-2021-7019367, 14 pages.
Extended European Search Report dated Dec. 2, 2022, in corresponding European Application No. 19889922.1, 7 pages.

* cited by examiner

IMPLANTABLE DEVICE

FIELD

The embodiments relate to the field of interventional medical devices, and in particular to an implantable device.

BACKGROUND

As a kind of meshed/tubular implantable medical device, the intravascular stent can be used in the treatment of various vascular diseases. An intravascular stent is implanted into a lesion segment to support the stenosed and occluded blood vessels, thus reducing the elastic retraction and reshaping of the blood vessels, while maintaining a smooth lumen blood flow.

Intravascular stents are generally made from metal or high polymer materials. An intravascular stent is generally cut or braided into a desired shape, and then crimped to a delivery balloon or a delivery sheath to be fixed in a delivery system; during such process, the stent may reduce 50% above in its outer diameter and experiences large deformation. The intravascular stent is released and expanded after being delivered to the lesion; during such process, the intravascular stent is expanded 200% above in its outer diameter again and experiences larger deformation. The intravascular stent undergoes repeated large deformations during the crimping and expansion process. Moreover, the stent will be buckled, stretched, and even twisted along with the movement, contraction, and relaxation of blood vessels after being implanted in the body; that is, the stent bears periodic loads (such as radial pulsation squeezing, axial tension and buckling) in blood vessels, which demands for high plastic deformation capacity of the stent. However, the existing stent lacks sufficient plastic deformation capacity, resulting in fracture due to fatigue after implantation, and even fracture during expansion. The fracture will cause undesirable consequences: on the one hand, the fractured stent strut will cause local mechanical vascular stimulation, resulting in inflammation and neointimal hyperplasia; on the other hand, the fractured stent strut will damage the local stent structure, resulting in thrombosis and blood flow blockage, thereby affecting the blood flow supply of organs. The above undesirable consequences may not only cause the loss of the radial support performance of the local stent region, thus making it difficult to play the role of radial support, but also may bring great clinical risks to the patient.

The plastic deformation capacity of the intravascular stent is mainly related to its structural design and stent material; and when the structural design of the stent is determined, the plastic deformation capacity of the material itself will play a greater role. The plastic deformation capacity of a metal-substrate material depends on its microstructure which includes grain size and orientation, metallographic structure, second phase particles, dislocation structure and the like. The plastic deformation capacity greatly varies from different microstructures, and thus can be optimized by optimizing the microstructure.

SUMMARY

In view of this, it is necessary to provide an implantable device having good plastic deformation capacity.

Embodiments include an implantable device, including a metal substrate containing particles having a size of 1 μm above, whereZ:

if the wall thickness of the metal substrate is greater than or equal to 0.04 mm and less than or equal to 0.12 mm, the largest size of the particles is less than or equal to 15 μm and the average content of the particles is less than or equal to 40 ppm;

if the wall thickness of the metal substrate is greater than 0.12 mm and less than or equal to 0.2 mm, the largest size of the particles is less than or equal to 20 μm and the average content of the particles is less than or equal to 100 ppm;

and if the wall thickness of the metal substrate is greater than 0.2 mm and less than or equal to 0.3 mm, the largest size of the particles is less than or equal to 25 μm and the average content of the particles is less than or equal to 220 ppm.

In one embodiment, if the wall thickness of the metal substrate is greater than or equal to 0.04 mm and less than or equal to 0.12 mm, the largest size of the particles is less than or equal to 10 μm and the average content of the particles is less than or equal to 40 ppm;

if the wall thickness of the metal substrate is greater than 0.12 mm and less than or equal to 0.2 mm, the largest size of the particles is less than or equal to 15 μm and the average content of the particles is less than or equal to 100 ppm;

and if the wall thickness of the metal substrate is greater than 0.2 mm and less than or equal to 0.3 mm, the largest size of the particles is less than or equal to 20 μm and the average content of the particles is less than or equal to 220 ppm.

In one embodiment, if the wall thickness of the metal substrate is greater than or equal to 0.04 mm and less than or equal to 0.12 mm, the largest size of the particles is less than or equal to 10 μm and the average content of the particles is less than or equal to 20 ppm;

if the wall thickness of the metal substrate is greater than 0.12 mm and less than or equal to 0.2 mm, the largest size of the particles is less than or equal to 15 μm and the average content of the particles is less than or equal to 50 ppm;

and if the wall thickness of the metal substrate is greater than 0.2 mm and less than or equal to 0.3 mm, the largest size of the particles is less than or equal to 20 μm and the average content of the particles is less than or equal to 110 ppm.

In one embodiment, if the wall thickness of the metal substrate is greater than or equal to 0.04 mm and less than or equal to 0.12 mm, the largest size of the particles is less than or equal to 15 μm; and if the theoretical over-expansion capacity of the metal substrate ranges from 25% to 45%, the average content of the particles is less than or equal to 20 ppm;

if the wall thickness of the metal substrate is greater than or equal to 0.04 mm and less than or equal to 0.12 mm, the largest size of the particles is less than or equal to 15 μm; and if the theoretical over-expansion capacity of the metal substrate is greater than 45%, the average content of the particles is less than or equal to 40 ppm;

if the wall thickness of the metal substrate is greater than 0.12 mm and less than or equal to 0.2 mm, the largest size of the particles is less than or equal to 20 μm; and if the theoretical over-expansion capacity of the metal substrate ranges from 25% to 45%, the average content of the particles is less than or equal to 50 ppm;

if the wall thickness of the metal substrate is greater than 0.12 mm and less than or equal to 0.2 mm, the largest size of the particles is less than or equal to 20 μm; and if the theoretical over-expansion capacity of the metal substrate is greater than 45%, the average content of the particles is less than or equal to 100 ppm;

if the wall thickness of the metal substrate is greater than 0.2 mm and less than or equal to 0.3 mm, the largest size of the particles is less than or equal to 25 μm; and if the theoretical over-expansion capacity of the metal substrate ranges from 25% to 45%, the average content of the particles is less than or equal to 110 ppm;

and if the wall thickness of the metal substrate is greater than 0.2 mm and less than or equal to 0.3 mm, the largest size of the particles is less than or equal to 25 μm; and if the theoretical over-expansion capacity of the metal substrate is greater than 45%, the average content of the particles is less than or equal to 220 ppm.

In one embodiment, if the wall thickness of the metal substrate is greater than or equal to 0.04 mm and less than or equal to 0.12 mm, the largest size of the particles is less than or equal to 15 μm; and if the theoretical over-expansion capacity of the metal substrate ranges from 25% to 45%, the average content of the particles is less than or equal to 10 ppm;

if the wall thickness of the metal substrate is greater than or equal to 0.04 mm and less than or equal to 0.12 mm, the largest size of the particles is less than or equal to 15 μm; and if the theoretical over-expansion capacity of the metal substrate is greater than 45%, the average content of the particles is less than or equal to 20 ppm;

if the wall thickness of the metal substrate is greater than 0.12 mm and less than or equal to 0.2 mm, the largest size of the particles is less than or equal to 20 μm; and if the theoretical over-expansion capacity of the metal substrate ranges from 25% to 45%, the average content of the particles is less than or equal to 25 ppm;

if the wall thickness of the metal substrate is greater than 0.12 mm and less than or equal to 0.2 mm, the largest size of the particles is less than or equal to 20 μm; and if the theoretical over-expansion capacity of the metal substrate is greater than 45%, the average content of the particles is less than or equal to 50 ppm;

if the wall thickness of the metal substrate is greater than 0.2 mm and less than or equal to 0.3 mm, the largest size of the particles is less than or equal to 25 μm; and if the theoretical over-expansion capacity of the metal substrate ranges from 25% to 45%, the average content of the particles is less than or equal to 55 ppm; and if the wall thickness of the metal substrate is greater than 0.2 mm and less than or equal to 0.3 mm, the largest size of the particles is less than or equal to 25 μm; and if the theoretical over-expansion capacity of the metal substrate is greater than 45%, the average content of the particles is less than or equal to 110 ppm.

In one embodiment, if the wall thickness of the metal substrate is greater than or equal to 0.04 mm and less than or equal to 0.12 mm, the largest size of the particles is less than or equal to 10 μm; and if the theoretical over-expansion capacity of the metal substrate ranges from 25% to 45%, the average content of the particles is less than or equal to 10 ppm;

if the wall thickness of the metal substrate is greater than or equal to 0.04 mm and less than or equal to 0.12 mm, the largest size of the particles is less than or equal to 10 μm; and if the theoretical over-expansion capacity of the metal substrate is greater than 45%, the average content of the particles is less than or equal to 20 ppm;

if the wall thickness of the metal substrate is greater than 0.12 mm and less than or equal to 0.2 mm, the largest size of the particles is less than or equal to 15 μm; and if the theoretical over-expansion capacity of the metal substrate ranges from 25% to 45%, the average content of the particles is less than or equal to 25 ppm;

if the wall thickness of the metal substrate is greater than 0.12 mm and less than or equal to 0.2 mm, the largest size of the particles is less than or equal to 15 μm; and if the theoretical over-expansion capacity of the metal substrate is greater than 45%, the average content of the particles is less than or equal to 50 ppm;

if the wall thickness of the metal substrate is greater than 0.2 mm and less than or equal to 0.3 mm, the largest size of the particles is less than or equal to 20 μm; and if the theoretical over-expansion capacity of the metal substrate ranges from 25% to 45%, the average content of the particles is less than or equal to 55 ppm; and if the wall thickness of the metal substrate is greater than 0.2 mm and less than or equal to 0.3 mm, the largest size of the particles is less than or equal to 20 μm; and if the theoretical over-expansion capacity of the metal substrate is greater than 45%, the average content of the particles is less than or equal to 110 ppm.

In one embodiment, the material of the metal substrate could be nitrided iron, pure iron, cobalt-chromium alloys and magnesium alloys.

In one embodiment, the implantable device could be an intravascular stent, a biliary stent, an esophageal stent, or a urethral stent.

In one embodiment, the intravascular stent could be a coronary stent or a peripheral vascular stent.

In one embodiment, the metal substrate material is prepared by electroslag remelting and then vacuum arc melting.

Experiments related to the embodiments prove that reasonable control of the size and the average content of the particles according to the wall thickness of the metal substrate of the implant device can optimize the microstructure of the metal substrate, which is beneficial to the improvement in the plastic deformation capacity of the implantable device, thus reducing the risk of abnormal fracture of the implantable device.

DETAILED DESCRIPTION OF THE EMBODIMENTS

For the convenience of understanding, the embodiments will be described more comprehensively with reference to the accompanying drawings. Embodiments are shown in the accompanying drawings. The embodiments may, however, be embodied in many different forms and should not be construed as limited to the embodiments set forth herein. Rather, these embodiments are exemplary and non-limiting.

Unless defined otherwise, all terms used herein have the same meanings as commonly understood by a person of ordinary skill in the art to which the embodiments belong. The terms used in the description of the embodiments herein are for the purpose of describing particular embodiments merely and are not limiting. As used herein, the term "and/or" includes any and all combinations of one or more of the associated items listed.

The particle size referred to herein is the maximum distance of two points on the edge of the particles within the same plane.

An implantable device in one embodiment is an intravascular stent, a biliary stent, an esophageal stent, or a urethral stent. In one embodiment, the intravascular stent is a coronary stent or a peripheral vascular stent.

Figure 1:
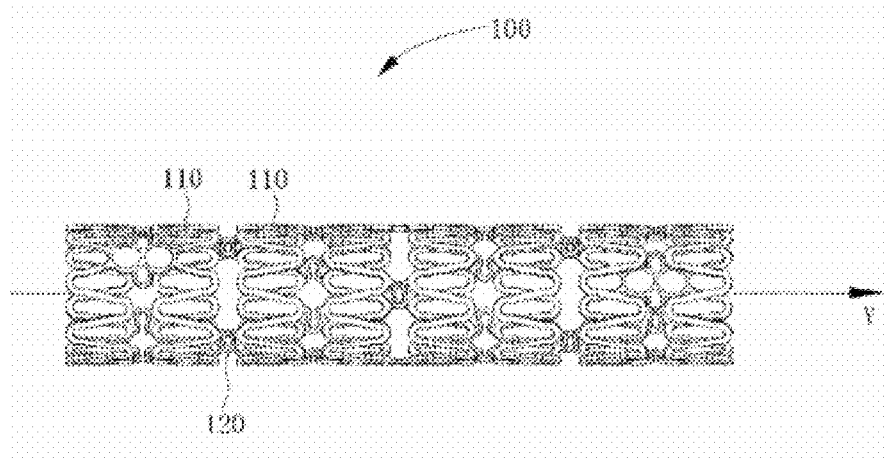
FIG. 1 is a structure diagram of a metal substrate of an implantable device in one embodiment.

As shown in FIG. 1, the implantable device includes a metal substrate 100; and the metal substrate 100 is a hollowed-out lumen structure.

Figure 2:
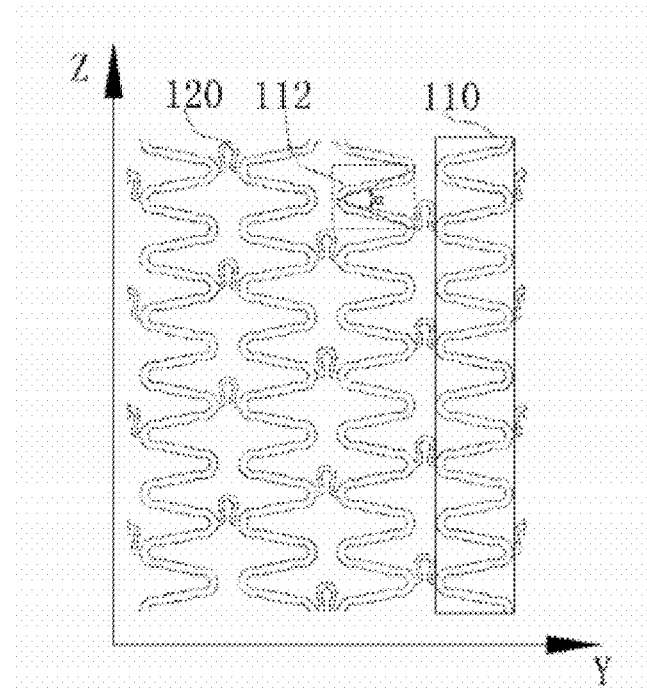
FIG. 2 is a schematic diagram showing the axial expansion of the metal substrate of the implantable device shown in FIG. 1.

Referring to FIG. 2 together, the metal substrate 100 includes a plurality of wave rings 110 arranged in an axial direction Y and connecting members 120 connecting two adjacent wave rings 110. Each wave ring 110 includes a plurality of waveform structures 112 arranged in a circumferential direction Z.

The metal substrate 100 is made of a metal material. In one embodiment, the material of the metal substrate 100 is one of nitrided iron, pure iron, cobalt-chromium alloys, and magnesium alloys. It can be appreciated that in other embodiments, the metal substrate 100 may be made of other metals or alloys beyond those listed above; and any metal or alloy capable of satisfying the requirements of the implantable device and biocompatible with organisms well may be used.

The material for forming the metal substrate 100 contains a plurality of particles, resulting in the formation of a plurality of particles within the metal substrate 100; and the particle size is greater than or equal to 1 μm. The particles include inclusions introduced externally, endogenous inclusions or a secondary phase as well. The particles may be from foreign substances introduced in the smelting process of a metal material. For example, a desoxidant is added to in a steel material to produce oxides and silicates during smelting; and sulfides and nitrides are formed in the solidification process of steel due to the decrease of the solubility of certain elements (such as sulfur and nitrogen); and these particles cannot be discharged in time and remain in the steel. It is difficult to achieve complete avoidance of particles, and at the same time, due to the random distribution, it is difficult to accurately control the distribution of these particles.

The size and content of the particles may adversely affect the microstructure of the metal substrate 100, thereby deteriorating the plastic deformation capacity of the metal substrate 100 to some extent. The extent of the deterioration mainly depends on the distribution and the size of the particles. The distribution of the particles in the severely deformed region of the metal substrate 100 is more likely to cause abnormal fracture of the implantable device. The larger the size of the particles is, the more serious the damage to the material continuity is; accordingly, it is more likely to cause the abnormal fracture of the implantable device. Thus, the particles can be controlled to reduce the risk of fracture of the implantable device. Therefore, it is necessary to reduce the amount of the particles, since the lower the amount of the particles is, the smaller the distribution probability of the particles in the deformation regions of the implantable device is; accordingly, it is less harmful.

The smaller the size of the particles is, the lower the damage to the material continuity is; and accordingly, it is less harmful. Moreover, the smaller the size of the implantable device is, the smaller the size of the particles should be, especially in the field of intravascular stents. At present, the thin-walled design may be preferred; and moreover, it may be more necessary to control the size of the particles when the wall thickness is thinner. It has been found that when the size of the particles in metal-based materials is less than 1 μm, these sub-micron or nano particles have little effect on the plastic deformation capacity of the material, and even can enhance the plastic deformation capacity to improve the strength of the material. But when the size of the particles is 1 μm or more, the particles will break the continuity of the material, possibly resulting in a decrease in the plasticity, toughness, and fatigue properties of the material. If these particles are present in the deformation sites of the metal substrate 100, it is rather likely to cause abnormal fracture (e.g., fracture during expansion) of the metal substrate 100 at these sites. Therefore, it is necessary to control the size and content of particles having a size of 1 μm or more.

In one embodiment, if the wall thickness of the metal substrate 100 is greater than or equal to 0.04 mm and less than or equal to 0.12 mm, the largest particle size is less than or equal to 15 μm and the average content of the particles is less than or equal to 40 ppm.

If the wall thickness of the metal substrate 100 is greater than 0.12 mm and less than or equal to 0.2 mm, the largest particle size is less than or equal to 20 μm and the average content of the particles is less than or equal to 100 ppm.

If the wall thickness of the metal substrate 100 is greater than 0.2 mm and less than or equal to 0.3 mm, the largest particle size is less than or equal to 25 μm and the average content of the particles is less than or equal to 220 ppm.

In one embodiment, if the wall thickness of the metal substrate 100 is greater than or equal to 0.04 mm and less than or equal to 0.12 mm, the largest particle size is less than or equal to 10 μm and the average content of the particles is less than or equal to 40 ppm.

If the wall thickness of the metal substrate 100 is greater than 0.12 mm and less than or equal to 0.2 mm, the largest particle size is less than or equal to 15 μm and the average content of the particles is less than or equal to 100 ppm.

If the wall thickness of the metal substrate 100 is greater than 0.2 mm and less than or equal to 0.3 mm, the largest particle size is less than or equal to 20 μm and the average content of the particles is less than or equal to 220 ppm.

In one embodiment, if the wall thickness of the metal substrate 100 is greater than or equal to 0.04 mm and less than or equal to 0.12 mm, the largest particle size is less than or equal to 10 μm and the average content of the particles is less than or equal to 20 ppm.

If the wall thickness of the metal substrate 100 is greater than 0.12 mm and less than or equal to 0.2 mm, the largest particle size is less than or equal to 15 μm and the average content of the particles is less than or equal to 50 ppm.

If the wall thickness of the metal substrate 100 is greater than 0.2 mm and less than or equal to 0.3 mm, the largest particle size is less than or equal to 20 μm and the average content of the particles is less than or equal to 110 ppm.

In one embodiment, if the wall thickness of the metal substrate 100 is greater than or equal to 0.04 mm and less than or equal to 0.12 mm, the largest particle size is less than or equal to 15 μm; and if the theoretical over-expansion capacity of the metal substrate 100 ranges from 25% to 45%, the average content of the particles is less than or equal to 20 ppm.

If the wall thickness of the metal substrate is greater than or equal to 0.04 mm and less than or equal to 0.12 mm, the largest particle size is less than or equal to 15 μm; and if the theoretical over-expansion capacity of the metal substrate 100 is greater than 45%, the average content of the particles is less than or equal to 40 ppm.

If the wall thickness of the metal substrate 100 is greater than 0.12 mm and less than or equal to 0.2 mm, the largest particle size is less than or equal to 20 μm; and if the theoretical over-expansion capacity of the metal substrate 100 ranges from 25% to 45%, the average content of the particles is less than or equal to 50 ppm.

If the wall thickness of the metal substrate 100 is greater than 0.12 mm and less than or equal to 0.2 mm, the largest particle size is less than or equal to 20 μm; and if the theoretical over-expansion capacity of the metal substrate 100 is greater than 45%, the average content of the particles is less than or equal to 100 ppm.

If the wall thickness of the metal substrate 100 is greater than 0.2 mm and less than or equal to 0.3 mm, the largest particle size is less than or equal to 25 μm; and if the theoretical over-expansion capacity of the metal substrate 100 ranges from 25% to 45%, the average content of the particles is less than or equal to 110 ppm.

If the wall thickness of the metal substrate 100 is greater than 0.2 mm and less than or equal to 0.3 mm, the largest particle size is less than or equal to 25 μm; and if the theoretical over-expansion capacity of the metal substrate 100 is greater than 45%, the average content of the particles is less than or equal to 220 ppm.

In one embodiment, if the wall thickness of the metal substrate 100 is greater than or equal to 0.04 mm and less than or equal to 0.12 mm, the largest particle size is less than or equal to 15 μm; and if the theoretical over-expansion capacity of the metal substrate 100 ranges from 25% to 45%, the average content of the particles is less than or equal to 10 ppm.

If the wall thickness of the metal substrate 100 is greater than or equal to 0.04 mm and less than or equal to 0.12 mm, the largest particle size is less than or equal to 15 μm; and if the theoretical over-expansion capacity of the metal substrate 100 is greater than 45%, the average content of the particles is less than or equal to 20 ppm.

If the wall thickness of the metal substrate 100 is greater than 0.12 mm and less than or equal to 0.2 mm, the largest particle size is less than or equal to 20 μm; and if the theoretical over-expansion capacity of the metal substrate 100 ranges from 25% to 45%, the average content of the particles is less than or equal to 25 ppm.

If the wall thickness of the metal substrate 100 is greater than 0.12 mm and less than or equal to 0.2 mm, the largest particle size is less than or equal to 20 μm; and if the theoretical over-expansion capacity of the metal substrate 100 is greater than 45%, the average content of the particles is less than or equal to 50 ppm.

If the wall thickness of the metal substrate 100 is greater than 0.2 mm and less than or equal to 0.3 mm, the largest particle size is less than or equal to 25 μm; and if the theoretical over-expansion capacity of the metal substrate 100 ranges from 25% to 45%, the average content of the particles is less than or equal to 55 ppm.

If the wall thickness of the metal substrate 100 is greater than 0.2 mm and less than or equal to 0.3 mm, the largest particle size is less than or equal to 25 μm; and if the theoretical over-expansion capacity of the metal substrate 100 is greater than 45%, the average content of the particles is less than or equal to 110 ppm.

In one embodiment, if the wall thickness of the metal substrate 100 is greater than or equal to 0.04 mm and less than or equal to 0.12 mm, the largest particle size is less than or equal to 10 μm; and if the theoretical over-expansion capacity of the metal substrate 100 ranges from 25% to 45%, the average content of the particles is less than or equal to 10 ppm.

If the wall thickness of the metal substrate 100 is greater than or equal to 0.04 mm and less than or equal to 0.12 mm, the largest particle size is less than or equal to 10 μm; and if the theoretical over-expansion capacity of the metal substrate 100 is greater than 45%, the average content of the particles is less than or equal to 20 ppm.

If the wall thickness of the metal substrate 100 is greater than 0.12 mm and less than or equal to 0.2 mm, the largest particle size is less than or equal to 15 μm; and if the theoretical over-expansion capacity of the metal substrate 100 ranges from 25% to 45%, the average content of the particles is less than or equal to 25 ppm.

If the wall thickness of the metal substrate 100 is greater than 0.12 mm and less than or equal to 0.2 mm, the largest particle size is less than or equal to 15 μm; and if the theoretical over-expansion capacity of the metal substrate 100 is greater than 45%, the average content of the particles is less than or equal to 50 ppm.

If the wall thickness of the metal substrate 100 is greater than 0.2 mm and less than or equal to 0.3 mm, the largest particle size is less than or equal to 20 μm; and if the theoretical over-expansion capacity of the metal substrate 100 ranges from 25% to 45%, the average content of the particles is less than or equal to 55 ppm.

If the wall thickness of the metal substrate 100 is greater than 0.2 mm and less than or equal to 0.3 mm, the largest particle size is less than or equal to 20 μm; and if the theoretical over-expansion capacity of the metal substrate 100 is greater than 45%, the average content of the particles is less than or equal to 110 ppm.

N is defined as the theoretical over-expansion capacity of the metal substrate 100; L is defined as the length of a wave ring 110 of the metal substrate 100 after being straightened completely; and D is defined as the nominal outside diameter of the metal substrate 100, $$N = \frac{\frac{L}{\pi} - D}{D} \times 100\%;$$

where the nominal outside diameter is the nominal diameter of the metal substrate 100 plus double wall thickness. The nominal diameter refers to the inner diameter (the inner diameter of the metal substrate 100 after implantation in a blood vessel and expansion) of the metal substrate 100 after expansion. The nominal diameter is expressed in stent specifications terminology, for example, a 30008 stent, the nominal diameter is 3 mm and the nominal length is 8 mm after expansion; a 27538 stent, the nominal diameter is 2.75 mm and the nominal length is 38 mm after expansion; a 35015 stent, the nominal diameter is 3.5 mm and the nominal length is 15 mm after expansion.

The average content of the particles in the metal substrate 100 is the area occupied by the particles in per unit area of the metal substrate 100. That is, the average content of the particles in the metal substrate 100 is equal to the area occupied by the particles in a detection zone/the area of the detection zone; where the area of the detection zone is the total area of the detection zone; and the area occupied by the particles in the detection zone refers to the area occupied by the particles in a detection zone having a detection area of 10 mm² above randomly detected by an SEM at 500 magnifications. At least two detection zones are provided and are respectively distributed on two mutually perpendicular planes of the metal substrate 100; and the detection area on each detection zone is 5 mm$^2$ or more; that is, the average content of the particles is equal to the total area occupied by the particles in a plurality of detection zones/the total area of the plurality of detection zones.

The greater the size of the particles is, the higher the number of the particles is, and the larger the area of the particles on the metal substrate 100 per unit area is. When the average content of the particles is constant, the amount of the particles is less if the particle size is larger, so that the probability of the particles present in the critical deformation sites is small and its deterioration to the plastic deformation of the implantable device is weak. However, when the average content of the particles is constant, the particle size is small if the amount of the particles is higher; even though the particles are present in the critical deformation sites, the deterioration to the plastic deformation of the implantable device is weak. Therefore, the size and the content of the particles are reasonably controlled, so as to avoid the adverse effects of the particles on the plastic deformation capacity of the implantable device.

In one embodiment, the material of the metal substrate 100 is prepared by at least one of electroslag remelting and vacuum arc melting. Particles of the metal substrate 100 is mainly from raw materials thereof; and the level (size and average content) of the particles is not substantially affected during the preparation of the metal substrate 100. Therefore, there is a need to control the level of the particles in the raw material. Electroslag remelting and vacuum arc melting can improve the purity of the metal material, reduce the level of the particles in the metal material, and can optimize the microstructure of the metal material, thereby optimizing the plastic deformation capacity of the metal material.

Electroslag remelting is a process that an electrode is molten by resistance heat generated by electric current through molten slag as a heat source, and then the molten metal is gathered drops into a metallic bath after through a slag layer; during passing through the slag layer, nonmetallic inclusions are absorbed by the slag, and harmful elements (phosphorus, sulfur, lead, stibium, bismuth, tin and the like) are effectively removed through steel-slag reaction and high-temperature vaporization, so that the steel ingots are purified and finally solidified into castings in a water cooled crystallizer.

Vacuum arc melting refers to a smelting process that a material to be smelted serves as an electrode and a water-cooled copper crucible serves as another electrode, and then arc strike is conducted between the two electrodes; and then the material to be smelted is molten by high temperature of the arc, dropping in the crucible, then gradually molten and condensed into an ingot. Vacuum melting can significantly remove hydrogen and other volatile impurities and can obviously reduce the content of the particles through a floating effect.

In one embodiment, the material of metal substrate 100 is prepared by electroslag remelting and then vacuum arc melting. The material is firstly processed by electroslag remelting, and then further purified through vacuum arc melting, thus facilitating the reduction of the content of the particles.

The size and the average content of the particles are reasonably controlled based on the wall thickness of the metal substrate 100 of the implantable device. It has been determined from tests that the embodiments can effectively avoid the adverse effects of the particles in the material on the microstructure of the metal substrate 100, thus facilitating the improvement of the plastic deformation capacity of the implantable device to reduce the risk of abnormal fracture of the implantable device.

Further, the size and the average content of the particles are rationally controlled based on the wall thickness and theoretical over-expansion capacity of the metal substrate 100, thus further optimizing the microstructure of the metal substrate 100, thereby enhancing the plastic deformation capacity of the implantable device.

Examples are provided hereafter (coronary stents and peripheral vascular stents are set as examples below to further describe the above implantable device, but the protection scope of the embodiments is not limited thereto).

The particles referred to in the following examples are particles having a size of 1 μm or more. Samples in the following examples were prepared as follows: materials were ground and polished on an ECO Met 250 semi-automatic polisher manufactured by BRUKER to obtain sections having shiny mirror surfaces, and then the sections were observed under a scanning electron microscope; or the samples were placed in liquid nitrogen for brittle fracture to obtain sections, and then the sections were observed under a scanning electron microscope at 500 magnifications.

An expansion test served to assess the influences of the particles on the plastic deformation capacity of the stent. A portion of raw materials were randomly selected and prepared into three tubes or three wires and the like to prepare intravascular stents; the length of the tubes or wires prepared from the selected raw materials should be not less than 1.0 m. These tubes or wires were made into stents for over-expansion test as much as possible under the permission of the process conditions; that is, the stents were expanded until fracture; afterwards, the fracture was observed under an SEM produced by a Japanese Cooperation. If no particles were found on the fracture, it was indicated that the fracture of the sent was not affected by the particles; that is, the plastic deformation capacity of the stent was not seriously deteriorated by the particles in the material.

Example 1

The raw material was nitrided iron, and the nitrided iron was prepared by electroslag remelting and then vacuum arc melting. A portion of the raw material was randomly cut, ground and polished to obtain a bright section with an observed area of 15 mm$^2$. The result was as follows: the largest particle size was 5 μm and the average content of particles was 5 ppm. A portion of the raw material was randomly selected and made into 3 tubes (length was 1.0 m) to be prepared into a coronary stent having a wall thickness of 0.040 mm and theoretical over-expansion capacity of 60%.

The prepared coronary stent was subjected to an expansion test, and no particles were found on the fracture.

Example 2

The raw material was nitrided iron and prepared by electroslag remelting. A portion of the material was randomly cut, ground and polished to obtain a bright section with an observed area of 10 mm$^2$. The result was as follows: the largest particle size was 10 μm and the average content of particles was 10 ppm. A portion of the raw material was randomly selected and made into 3 tubes (length was 1.2 m)

to be prepared into a coronary stent having a wall thickness of 0.053 mm and theoretical over-expansion capacity of 51%.

The prepared coronary stent was subjected to an expansion test, and no particles were found on the fracture.

Example 3

The raw material was pure iron and prepared by vacuum arc melting. The raw material was placed in liquid nitrogen for brittle fracture to obtain a section having an observed area of 12 mm². The result was as follows: the largest particle size was 10 μm and the average content of particles was 40 ppm. A portion of the raw material was randomly selected and made into 3 tubes (length was 1.5 m) to be prepared into a coronary stent having a wall thickness of 0.070 mm and theoretical over-expansion capacity of 65%.

The prepared coronary stent was subjected to an expansion test, and no particles were found on the fracture.

Example 4

The raw material was a cobalt-chromium alloy and prepared by electroslag remelting. A portion of the raw material was randomly cut, ground and polished to obtain a bright section with an observed area of 10 mm². The result was as follows: the largest particle size was 15 μm and the average content of particles was 20 ppm. A portion of the raw material was randomly selected and made into 3 tubes (length was 1.0 m) to be prepared into a coronary stent having a wall thickness of 0.080 mm and theoretical over-expansion capacity of 45%.

The prepared coronary stent was subjected to an expansion test, and no particles were found on the fracture.

Example 5

The raw material was nitrided iron, and the nitrided iron was prepared by electroslag remelting and then vacuum arc melting. A portion of the raw material was randomly cut, ground and polished to obtain a bright section with an observed area of 15 mm². The result was as follows: the largest particle size was 5 μm and the average content of particles was 10 ppm. A portion of the raw material was randomly selected and made into 3 tubes (length was 1.0 m) to be prepared into a coronary stent having a wall thickness of 0.090 mm and theoretical over-expansion capacity of 36%.

The prepared coronary stent was subjected to an expansion test, and no particles were found on the fracture.

Example 6

The raw material was nitrided iron and prepared by vacuum arc melting. A portion of the raw material was randomly cut, ground and polished to obtain a bright section with an observed area of 10 mm². The result was as follows: the largest particle size was 5 μm and the average content of particles was 10 ppm. A portion of the raw material was randomly selected and made into 3 tubes (length was 1.0 m) to be prepared into a coronary stent having a wall thickness of 0.100 mm and theoretical over-expansion capacity of 25%.

The prepared coronary stent was subjected to an expansion test, and no particles were found on the fracture.

Example 7

The raw material was a magnesium alloy and prepared by vacuum arc melting. A portion of the raw material was randomly cut, ground and polished to obtain a bright section with an observed area of 10 mm². The result was as follows: the largest particle size was 10 μm and the average content of particles was 20 ppm. A portion of the raw material was randomly selected and made into 3 tubes (length was 1.0 m) to be prepared into a coronary stent having a wall thickness of 0.120 mm and theoretical over-expansion capacity of 60%.

The prepared coronary stent was subjected to an expansion test, and no particles were found on the fracture.

Example 8

The raw material was nitrided iron and prepared by electroslag remelting. A portion of the raw material was randomly cut, ground and polished to obtain a bright section with an observed area of 10 mm². The result was as follows: the largest particle size was 10 μm and the average content of particles was 25 ppm. A portion of the raw material was randomly selected and made into 3 tubes (length was 1.0 m) to be prepared into a peripheral vascular stent having a wall thickness of 0.150 mm and theoretical over-expansion capacity of 40%.

The prepared peripheral vascular stent was subjected to an expansion test, and no particles were found on the fracture.

Example 9

The raw material was nitrided iron and prepared by electroslag remelting. A portion of the raw material was randomly cut, ground and polished to obtain a bright section with an observed area of 10 mm². The result was as follows: the largest particle size was 15 μm and the average content of particles was 50 ppm. A portion of the raw material was randomly selected and made into 3 tubes (length was 1.0 m) to be prepared into a peripheral vascular stent having a wall thickness of 0.180 mm and theoretical over-expansion capacity of 50%.

The prepared peripheral vascular stent was subjected to an expansion test, and no particles were found on the fracture.

Example 10

The raw material was a cobalt-chromium alloy and prepared by electroslag remelting. A portion of the raw material was randomly cut, ground and polished to obtain a bright section with an observed area of 10 mm². The result was as follows: the largest particle size was 15 μm and the average content of particles was 60 ppm. A portion of the raw material was randomly selected and made into 3 tubes (length was 1.0 m) to be prepared into a peripheral vascular stent having a wall thickness of 0.190 mm and theoretical over-expansion capacity of 45%.

The prepared peripheral vascular stent was subjected to an expansion test, and no particles were found on the fracture.

Example 11

The raw material was nitrided iron and prepared by electroslag remelting. A portion of the raw material was randomly cut, ground and polished to obtain a bright section with an observed area of 10 mm². The result was as follows: the largest particle size was 20 μm and the average content of particles was 100 ppm. A portion of the raw material was randomly selected and made into 3 tubes (length was 1.0 m)

to be prepared into a peripheral vascular stent having a wall thickness of 0.200 mm and theoretical over-expansion capacity of 65%.

The prepared peripheral vascular stent was subjected to an expansion test, and no particles were found on the fracture.

Example 12

The raw material was nitrided iron and prepared by electroslag remelting. A portion of the raw material was randomly cut, ground and polished to obtain a bright section with an observed area of 10 mm². The result was as follows: the largest particle size was 10 μm and the average content of particles was 30 ppm. A portion of the raw material was randomly selected and made into 3 tubes (length was 1.0 m) to be prepared into a peripheral vascular stent having a wall thickness of 0.200 mm and theoretical over-expansion capacity of 35%.

The prepared peripheral vascular stent was subjected to an expansion test, and no particles were found on the fracture.

Example 13

The raw material was pure iron and prepared by electroslag remelting. A portion of the raw material was randomly cut, ground and polished to obtain a bright section with an observed area of 10 mm². The result was as follows: the largest particle size was 15 μm and the average content of particles was 80 ppm. A portion of the raw material was randomly selected and made into 3 tubes (length was 1.0 m) to be prepared into a peripheral vascular stent having a wall thickness of 0.200 mm and theoretical over-expansion capacity of 65%.

The prepared peripheral vascular stent was subjected to an expansion test, and no particles were found on the fracture.

Example 14

The raw material was nitrided iron and prepared by electroslag remelting. A portion of the raw material was randomly cut, ground and polished to obtain a bright section with an observed area of 10 mm². The result was as follows: the largest particle size was 20 μm and the average content of particles was 55 ppm. A portion of the raw material was randomly selected and made into 3 tubes (length was 1.0 m) to be prepared into a peripheral vascular stent having a wall thickness of 0.230 mm and theoretical over-expansion capacity of 60%.

The prepared peripheral vascular stent was subjected to an expansion test, and no particles were found on the fracture.

Example 15

The raw material was nitrided iron and prepared by electroslag remelting. A portion of the raw material was randomly cut, ground and polished to obtain a bright section with an observed area of 10 mm². The result was as follows: the largest particle size was 15 μm and the average content of particles was 110 ppm. A portion of the raw material was randomly selected and made into 3 tubes (length was 1.0 m) to be prepared into a peripheral vascular stent having a wall thickness of 0.280 mm and theoretical over-expansion capacity of 50%.

The prepared peripheral vascular stent was subjected to an expansion test, and no particles were found on the fracture.

Example 16

The raw material was nitrided iron and prepared by electroslag remelting. A portion of the raw material was randomly cut, ground and polished to obtain a bright section with an observed area of 10 mm². The result was as follows: the largest particle size was 18 μm and the average content of particles was 40 ppm. A portion of the raw material was randomly selected and made into 3 tubes (length was 1.0 m) to be prepared into a peripheral vascular stent having a wall thickness of 0.290 mm and theoretical over-expansion capacity of 45%.

The prepared peripheral vascular stent was subjected to an expansion test, and no particles were found on the fracture.

Example 17

The raw material was nitrided iron and prepared by electroslag remelting. A portion of the raw material was randomly cut, ground and polished to obtain a bright section with an observed area of 10 mm². The result was as follows: the largest particle size was 10 μm and the average content of particles was 20 ppm. A portion of the raw material was randomly selected and made into 3 tubes (length was 1.0 m) to be prepared into a peripheral vascular stent having a wall thickness of 0.300 mm and theoretical over-expansion capacity of 25%.

The prepared peripheral vascular stent was subjected to an expansion test, and no particles were found on the fracture.

Example 18

The raw material was nitrided iron and prepared by electroslag remelting. A portion of the raw material was randomly cut, ground and polished to obtain a bright section with an observed area of 10 mm². The result was as follows: the largest particle size was 15 μm and the average content of particles was 60 ppm. A portion of the raw material was randomly selected and made into 3 tubes (length was 1.0 m) to be prepared into a peripheral vascular stent having a wall thickness of 0.300 mm and theoretical over-expansion capacity of 35%.

The prepared peripheral vascular stent was subjected to an expansion test, and no particles were found on the fracture.

Example 19

The raw material was nitrided iron and prepared by electroslag remelting. A portion of the raw material was randomly cut, ground and polished to obtain a bright section with an observed area of 10 mm². The result was as follows: the largest particle size was 25 μm and the average content of particles was 220 ppm. A portion of the raw material was randomly selected and made into 3 tubes (length was 1.0 m) to be prepared into a peripheral vascular stent having a wall thickness of 0.300 mm and theoretical over-expansion capacity of 65%.

The prepared peripheral vascular stent was subjected to an expansion test, and no particles were found on the fracture.

Comparative Example 1

The raw material was nitrided iron; and Comparative Example 1 differed from Example 2 in that the average content of the particles was 50 ppm. A portion of the raw material was randomly selected and made into 3 tubes (length was 1.2 m) to be prepared into a coronary stent the same as that in Example 2.

Figure 3:
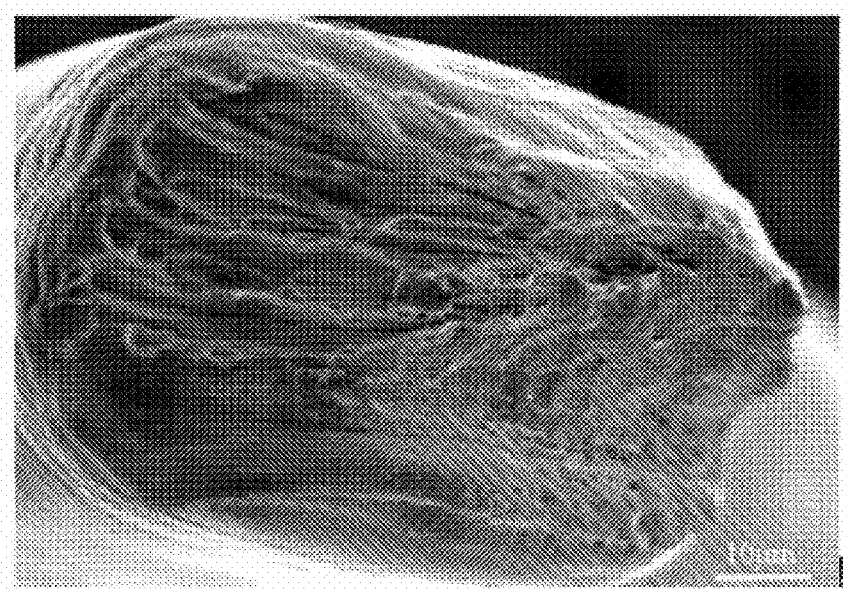
FIG. 3 is a scanning electron microscope (SEM) image showing a fracture of a coronary stent in Example 2.

The prepared coronary stent was subjected to an expansion test, and as a result, particles were found on 8 fractures of the coronary stent, as shown in FIG. 3, there were particles in the circle of FIG. 3.

Comparative Example 2

The raw material was nitrided iron; and Comparative Example 2 differed from Example 2 in that the largest particle size was 20 μm. A portion of the raw material was randomly selected and made into 3 tubes (length was 1.2 m) to be prepared into a coronary stent the same as that in Example 2.

Figure 4:
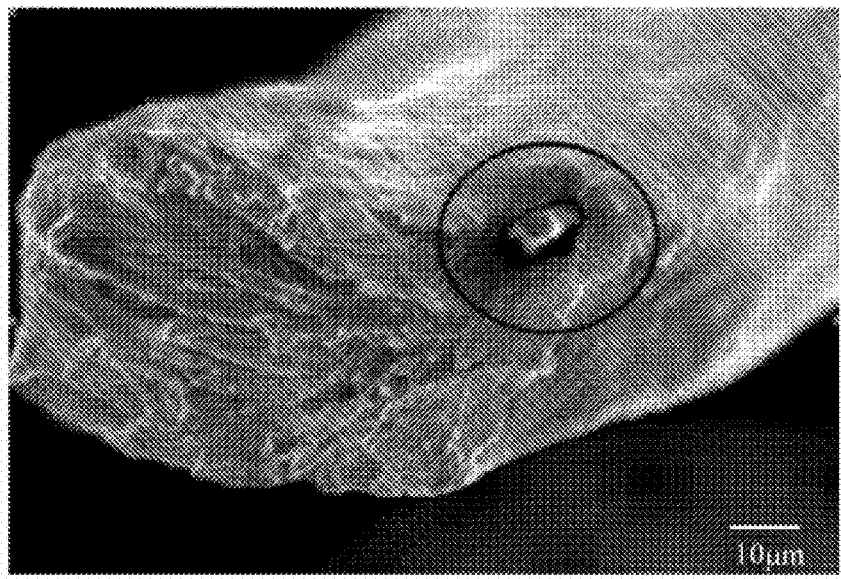
FIG. 4 is an SEM image showing a fracture of a coronary stent in Comparative Example 1.
Figure 5:
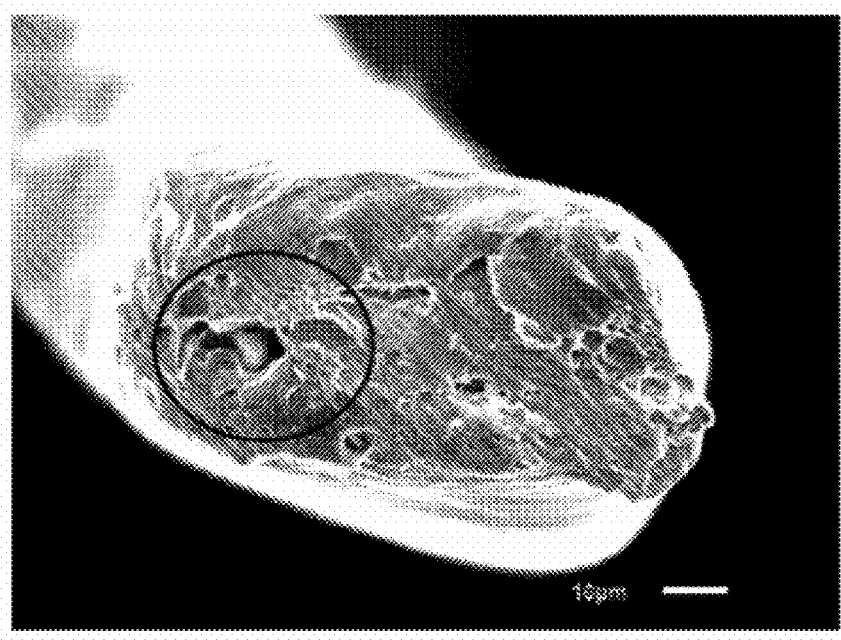
FIG. 5 is an SEM image showing a fracture of a coronary stent in Comparative Example 2.

The prepared coronary stent was subjected to an expansion test, and as a result, particles were found on 5 fractures of the coronary stent, as shown in FIG. 4, there were particles in the circle of FIG. 4.

Comparative Example 3

The raw material was nitrided iron, and the nitrided iron was prepared by electroslag remelting and then vacuum arc melting. A portion of the raw material was randomly cut, ground and polished to obtain a bright section with an observed area of 15 mm². The result was as follows: the largest particle size was 5 μm and the average content of particles was 25 ppm. A portion of the raw material was randomly selected and made into 3 tubes (length was 1.0 m) to be prepared into a coronary stent having a wall thickness of 0.090 mm and theoretical over-expansion capacity of 36%.

The prepared coronary stent was subjected to an expansion test, and as a result, particles were found on 6 fractures of the coronary stent.

Comparative Example 4

The raw material was nitrided iron, and the nitrided iron was prepared by electroslag remelting and then vacuum arc melting. A portion of the raw material was randomly cut, ground and polished to obtain a bright section with an observed area of 15 mm². The result was as follows: the largest particle size was 20 μm and the average content of particles was 10 ppm. A portion of the raw material was randomly selected and made into 3 tubes (length was 1.0 m) to be prepared into a coronary stent having a wall thickness of 0.090 mm and theoretical over-expansion capacity of 36%.

The prepared coronary stent was subjected to an expansion test, and as a result, particles were found on 4 fractures of the coronary stent.

Comparative Example 5

The raw material was nitrided iron and prepared by electroslag remelting. A portion of the raw material was randomly cut, ground and polished to obtain a bright section with an observed area of 10 mm². The result was as follows: the largest particle size was 15 μm and the average content of particles was 110 ppm. A portion of the raw material was randomly selected and made into 3 tubes (length was 1.0 m) to be prepared into a peripheral vascular stent having a wall thickness of 0.180 mm and theoretical over-expansion capacity of 50%.

The prepared peripheral vascular stent was subjected to an expansion test, and as a result, particles were found on 8 fractures of the peripheral vascular stent.

Comparative Example 6

The raw material was nitrided iron and prepared by electroslag remelting. A portion of the raw material was randomly cut, ground and polished to obtain a bright section with an observed area of 10 mm². The result was as follows: the largest particle size was 25 μm and the average content of particles was 50 ppm. A portion of the raw material was randomly selected and made into 3 tubes (length was 1.0 m) to be prepared into a peripheral vascular stent having a wall thickness of 0.180 mm and theoretical over-expansion capacity of 50%.

The prepared peripheral vascular stent was subjected to an expansion test, and as a result, particles were found on 8 fractures of the peripheral vascular stent.

Comparative Example 7

The raw material was nitrided iron and prepared by electroslag remelting. A portion of the raw material was randomly cut, ground and polished to obtain a bright section with an observed area of 10 mm². The result was as follows: the largest particle size was 10 μm and the average content of the particles was 55 ppm. A portion of the raw material was randomly selected and made into 3 tubes (length was 1.0 m) to be prepared into a peripheral vascular stent having a wall thickness of 0.200 mm and theoretical over-expansion capacity of 35%.

The prepared peripheral vascular stent was subjected to an expansion test, and as a result, particles were found on 7 fractures of the peripheral vascular stent.

Comparative Example 8

The raw material was nitrided iron and prepared by electroslag remelting. The material was prepared by electroslag remelting. A portion of the raw material was randomly cut, ground and polished to obtain a bright section with an observed area of 10 mm². The result was as follows: the largest particle size was 25 μm and the average content of the particles was 30 ppm. A portion of the raw material was randomly selected and made into 3 tubes (length was 1.0 m) to be prepared into a peripheral vascular stent having a wall thickness of 0.200 mm and theoretical over-expansion capacity of 35%.

The prepared peripheral vascular stent was subjected to an expansion test, and as a result, particles were found on 5 fractures of the peripheral vascular stent.

Comparative Example 9

The raw material was nitrided iron and prepared by electroslag remelting. A portion of the raw material was randomly cut, ground and polished to obtain a bright section with an observed area of 10 mm². The result was as follows: the largest particle size was 15 μm and the average content of the particles was 120 ppm. A portion of the raw material was randomly selected and made into 3 tubes (length was 1.0 m) to be prepared into a peripheral vascular stent having a wall thickness of 0.300 mm and theoretical over-expansion capacity of 35%.

The prepared peripheral vascular stent was subjected to an expansion test, and as a result, particles were found on 10 fractures of the peripheral vascular stent.

Comparative Example 10

The raw material was nitrided iron and prepared by electroslag remelting. A portion of the raw material was randomly cut, ground and polished to obtain a bright section with an observed area of 10 mm². The result was as follows:

the largest particle size was 30 µm and the average content of the particles was 60 ppm. A portion of the raw material was randomly selected and made into 3 tubes (length was 1.0 m) to be prepared into a peripheral vascular stent having a wall thickness of 0.300 mm and theoretical over-expansion capacity of 35%.

The prepared peripheral vascular stent was subjected to an expansion test, and as a result, particles were found on 8 fractures of the peripheral vascular stent.

Comparative Example 11

The raw material was nitrided iron and prepared by electroslag remelting. A portion of the raw material was randomly cut, ground and polished to obtain a bright section with an observed area of 10 mm$^2$. The result was as follows: the largest particle size was 15 µm and the average content of the particles was 230 ppm. A portion of the raw material was randomly selected and made into 3 tubes (length was 1.0 m) to be prepared into a peripheral vascular stent having a wall thickness of 0.280 mm and theoretical over-expansion capacity of 50%.

The prepared peripheral vascular stent was subjected to an expansion test, and as a result, particles were found on 8 fractures of the peripheral vascular stent.

Comparative Example 12

The raw material was nitrided iron and prepared by electroslag remelting. A portion of the raw material was randomly cut, ground and polished to obtain a bright section with an observed area of 10 mm$^2$. The result was as follows: the largest particle size was 30 µm and the average content of the particles was 110 ppm. A portion of the raw material was randomly selected and made into 3 tubes (length was 1.0 m) to be prepared into a peripheral vascular stent having a wall thickness of 0.280 mm and theoretical over-expansion capacity of 50%.

The prepared peripheral vascular stent was subjected to an expansion test, and as a result, particles were found on 8 fractures of the peripheral vascular stent.

It can be seen from the above examples and comparative examples that the level of the particles in the material is controlled based on the different wall thickness of intravascular stents to avoid or reduce the adverse effect of the particles on the plastic deformation capacity of the stent.

Compared with Comparative Example 1, the particles in Example 2 have a lower average content, small probability of occurrence in key deformation sites, and less adverse effect on the plastic deformation capacity of the stent; compared with Comparative Example 2, the particles in Example 2 have a smaller largest particle size and weaker deterioration to the plastic deformation capacity of the stent.

Compared with Comparative Example 3, the particles in Example 5 have a lower average content, small probability of occurrence in key deformation sites, and less adverse effect on the plastic deformation capacity of the stent; compared with Comparative Example 4, the particles in Example 5 have a smaller largest particle size, and weaker deterioration to the plastic deformation capacity of the stent.

Compared with Comparative Example 5, the particles in Example 9 have a lower average content, small probability of occurrence in key deformation sites, and less adverse effect on the plastic deformation capacity of the stent; compared with Comparative Example 6, the particles in Example 9 have a smaller largest particle size, and weaker deterioration to the plastic deformation capacity of the stent.

Compared with Comparative Example 7, the particles in Example 12 have a lower average content, small probability of occurrence in key deformation sites, and less adverse effect on the plastic deformation capacity of the stent; compared with Comparative Example 8, the particles in Example 12 have a smaller largest particle size, and weaker deterioration to the plastic deformation capacity of the stent.

Compared with Comparative Example 9, the particles in Example 18 have a lower average content, small probability of occurrence in key deformation sites, and less adverse effect on the plastic deformation capacity of the stent; compared with Comparative Example 10, the particles in Example 18 have a smaller largest particle size, and weaker deterioration to the plastic deformation capacity of the stent.

Compared with Comparative Example 11, the particles in Example 15 have a lower average content, small probability of occurrence in key deformation sites, and less adverse effect on the plastic deformation capacity of the stent; compared with Comparative Example 12, the particles in Example 15 have a smaller largest particle size, and weaker deterioration to the plastic deformation capacity of the stent.

The features of the above examples may be combined in any combination and are non-limiting. In order to simplify the description of the embodiments, all possible combinations of the features in the above examples are not described one by one. Moreover, the combinations of these features should fall within the scope of the embodiments as long as there is no discrepancy among the combinations thereof.

The examples set forth above merely represent several embodiments, and are described in greater detail but are not to be construed as limiting. It should be indicated that a person of ordinary skill in the art can further make numerous variations and improvements without departing from the spirit of the embodiments. Moreover, these variations and improvements fall within the protection scope of the embodiments.

The invention claimed is:

1. An implantable device, comprising:
a metal substrate, the metal substrate comprising particles having a size of 1 µm or more, wherein:
the metal substrate has a wall thickness ranging from 0.04 mm to 0.3 mm;
if the wall thickness of the metal substrate is greater than or equal to 0.04 mm and less than or equal to 0.12 mm, the largest size of the particles is less than or equal to 15 µm and an average content of the particles is less than or equal to 40 ppm;
if the wall thickness of the metal substrate is greater than 0.12 mm and less than or equal to 0.2 mm, the largest size of the particles is less than or equal to 20 µm and the average content of the particles is less than or equal to 100 ppm; and
if the wall thickness of the metal substrate is greater than 0.2 mm and less than or equal to 0.3 mm, the largest size of the particles is less than or equal to 25 µm and the average content of the particles is less than or equal to 220 ppm.

2. The implantable device according to claim 1, wherein, if the wall thickness of the metal substrate is greater than or equal to 0.04 mm and less than or equal to 0.12 mm, the largest size of the particles is less than or equal to 10 µm and the average content of the particles is less than or equal to 40 ppm;
if the wall thickness of the metal substrate is greater than 0.12 mm and less than or equal to 0.2 mm, the largest size of the particles is less than or equal to 15 μm and the average content of the particles is less than or equal to 100 ppm; and if the wall thickness of the metal substrate is greater than 0.2 mm and less than or equal to 0.3 mm, the largest size of the particles is less than or equal to 20 μm and the average content of the particles is less than or equal to 220 ppm.

3. The implantable device according to claim 1, wherein, if the wall thickness of the metal substrate is greater than or equal to 0.04 mm and less than or equal to 0.12 mm, the largest size of the particles is less than or equal to 10 μm and the average content of the particles is less than or equal to 20 ppm;

if the wall thickness of the metal substrate is greater than 0.12 mm and less than or equal to 0.2 mm, the largest size of the particles is less than or equal to 15 μm and the average content of the particles is less than or equal to 50 ppm; and if the wall thickness of the metal substrate is greater than 0.2 mm and less than or equal to 0.3 mm, the largest size of the particles is less than or equal to 20 μm and the average content of the particles is less than or equal to 110 ppm.

4. The implantable device according to claim 1, wherein, if the wall thickness of the metal substrate is greater than or equal to 0.04 mm and less than or equal to 0.12 mm, the largest size of the particles is less than or equal to 15 μm; and if the theoretical over-expansion capacity of the metal substrate ranges from 25% to 45%, the average content of the particles is less than or equal to 20 ppm;

if the wall thickness of the metal substrate is greater than or equal to 0.04 mm and less than or equal to 0.12 mm, the largest size of the particles is less than or equal to 15 μm; and if the theoretical over-expansion capacity of the metal substrate is greater than 45%, the average content of the particles is less than or equal to 40 ppm;

if the wall thickness of the metal substrate is larger than 0.12 mm and less than or equal to 0.2 mm, the largest size of the particles is smaller than or equal to 20 μm; and if the theoretical over-expansion capacity of the metal substrate ranges from 25% to 45%, the average content of the particles is less than or equal to 50 ppm;

if the wall thickness of the metal substrate is greater than 0.12 mm and less than or equal to 0.2 mm, the largest size of the particles is less than or equal to 20 μm; and if the theoretical over-expansion capacity of the metal substrate is greater than 45%, the average content of the particles is less than or equal to 100 ppm;

if the wall thickness of the metal substrate is greater than 0.2 mm and less than or equal to 0.3 mm, the largest size of the particles is less than or equal to 25 μm; and if the theoretical over-expansion capacity of the metal substrate ranges from 25% to 45%, the average content of the particles is less than or equal to 110 ppm; and if the wall thickness of the metal substrate is greater than 0.2 mm and less than or equal to 0.3 mm, the largest size of the particles is less than or equal to 25 μm; and if the theoretical over-expansion capacity of the metal substrate is greater than 45%, the average content of the particles is less than or equal to 220 ppm.

5. The implantable device according to claim 1, wherein, if the wall thickness of the metal substrate is greater than or equal to 0.04 mm and less than or equal to 0.12 mm, the largest size of the particles is less than or equal to 15 μm; and if the theoretical over-expansion capacity of the metal substrate ranges from 25% to 45%, the average content of the particles is less than or equal to 10 ppm;

if the wall thickness of the metal substrate is greater than or equal to 0.04 mm and less than or equal to 0.12 mm, the largest size of the particles is less than or equal to 15 μm; and if the theoretical over-expansion capacity of the metal substrate is greater than 45%, the average content of the particles is less than or equal to 20 ppm;

if the wall thickness of the metal substrate is greater than 0.12 mm and less than or equal to 0.2 mm, the largest size of the particles is less than or equal to 20 μm; and if the theoretical over-expansion capacity of the metal substrate ranges from 25% to 45%, the average content of the particles is greater than or equal to 25 ppm;

if the wall thickness of the metal substrate is greater than 0.12 mm and less than or equal to 0.2 mm, the largest size of the particles is less than or equal to 20 μm; and if the theoretical over-expansion capacity of the metal substrate is greater than 45%, the average content of the particles is less than or equal to 50 ppm;

if the wall thickness of the metal substrate is greater than 0.2 mm and less than or equal to 0.3 mm, the largest size of the particles is less than or equal to 25 μm; and if the theoretical over-expansion capacity of the metal substrate ranges from 25% to 45%, the average content of the particles is less than or equal to 55 ppm; and if the wall thickness of the metal substrate is greater than 0.2 mm and less than or equal to 0.3 mm, the largest size of the particles is less than or equal to 25 μm; and if the theoretical over-expansion capacity of the metal substrate is greater than 45%, the average content of the particles is less than or equal to 110 ppm.

6. The implantable device according to claim 1, wherein, if the wall thickness of the metal substrate is greater than or equal to 0.04 mm and less than or equal to 0.12 mm, the largest size of the particles is less than or equal to 10 μm; and if the theoretical over-expansion capacity of the metal substrate ranges from 25% to 45%, the average content of the particles is less than or equal to 10 ppm;

if the wall thickness of the metal substrate is greater than or equal to 0.04 mm and less than or equal to 0.12 mm, the largest size of the particles is less than or equal to 10 μm; and if the theoretical over-expansion capacity of the metal substrate is greater than 45%, the average content of the particles is less than or equal to 20 ppm;

if the wall thickness of the metal substrate is greater than 0.12 mm and less than or equal to 0.2 mm, the largest size of the particles is less than or equal to 15 μm; and if the theoretical over-expansion capacity of the metal substrate ranges from 25% to 45%, the average content of the particles is less than or equal to 25 ppm;

if the wall thickness of the metal substrate is greater than 0.12 mm and less than or equal to 0.2 mm, the largest size of the particles is less than or equal to 15 μm; and if the theoretical over-expansion capacity of the metal substrate is greater than 45%, the average content of the particles is less than or equal to 50 ppm;

if the wall thickness of the metal substrate is greater than 0.2 mm and less than or equal to 0.3 mm, the largest size of the particles is less than or equal to 20 μm; and if the theoretical over-expansion capacity of the metal substrate ranges from 25% to 45%, the average content of the particles is less than or equal to 55 ppm; and if the wall thickness of the metal substrate is greater than 0.2 mm and less than or equal to 0.3 mm, the largest size of the particles is less than or equal to 20 μm; and if the theoretical over-expansion capacity of the metal substrate is greater than 45%, the average content of the particles is less than or equal to 110 ppm.

7. The implantable device according to claim 1, wherein the material of the metal substrate is selected from one of: nitrided iron, pure iron, cobalt-chromium alloys, and magnesium alloys.

8. The implantable device according to claim 1, wherein the implantable device is an intravascular stent, a biliary stent, an esophageal stent, or a urethral stent.

9. The implantable device according to claim 8, wherein the intravascular stent is a coronary stent or a peripheral vascular stent.

10. The implantable device according to claim 1, wherein the material of the metal substrate is prepared by electroslag remelting and then vacuum arc melting.

\* \* \* \* \*